United States Patent [19]

Quate et al.

[11] 4,006,444
[45] Feb. 1, 1977

[54] ACOUSTIC IMAGING APPARATUS

[75] Inventors: Calvin F. Quate, Los Altos Hill; James A. Cunningham, Redondo Beach, both of Calif.

[73] Assignee: The Board of Trustees of Leland Stanford Junior University, Stanford, Calif.

[22] Filed: Feb. 12, 1974

[21] Appl. No.: 441,802

[52] U.S. Cl. .............. 340/15; 340/5 MP; 340/5 H; 73/67.5 H
[51] Int. Cl.² ........................ H04B 11/00
[58] Field of Search ........... 340/5 MP, 5 H, 15; 73/67.5 H; 250/365, 372, 373, 461, 484

[56] References Cited

UNITED STATES PATENTS

| 2,644,890 | 7/1953 | Hollihan | 250/462 |
| 3,137,837 | 6/1964 | Wreford | 340/5 MP |
| 3,168,659 | 2/1965 | Bayre et al. | 340/8 L |
| 3,400,363 | 2/1975 | Silverman | 343/17 |
| 3,559,115 | 2/1968 | De Vries | 333/72 |
| 3,576,521 | 4/1971 | Silverman | 340/5 H |
| 3,585,847 | 6/1971 | Brenden | 340/5 H |
| 3,586,859 | 6/1971 | Katz et al. | 250/461 |
| 3,663,813 | 5/1972 | Shaw | 250/365 |
| 3,812,454 | 5/1974 | Bhuta et al. | 340/5 MP |

Primary Examiner—Maynard R. Wilbur
Assistant Examiner—T. M. Blum
Attorney, Agent, or Firm—Paul B. Fihe

[57] ABSTRACT

Acoustic imaging apparatus wherein a beam of high frequency acoustic energy is directed to the object to be imaged to create variations in the transmitted acoustic energy which variations are then detected by a plurality of small particles suspended in the beam path for motion in response to radiation pressure produced by the incident acoustic energy, thus providing a visible image with high contrast sensitivity and excellent image resolution.

1 Claim, 6 Drawing Figures

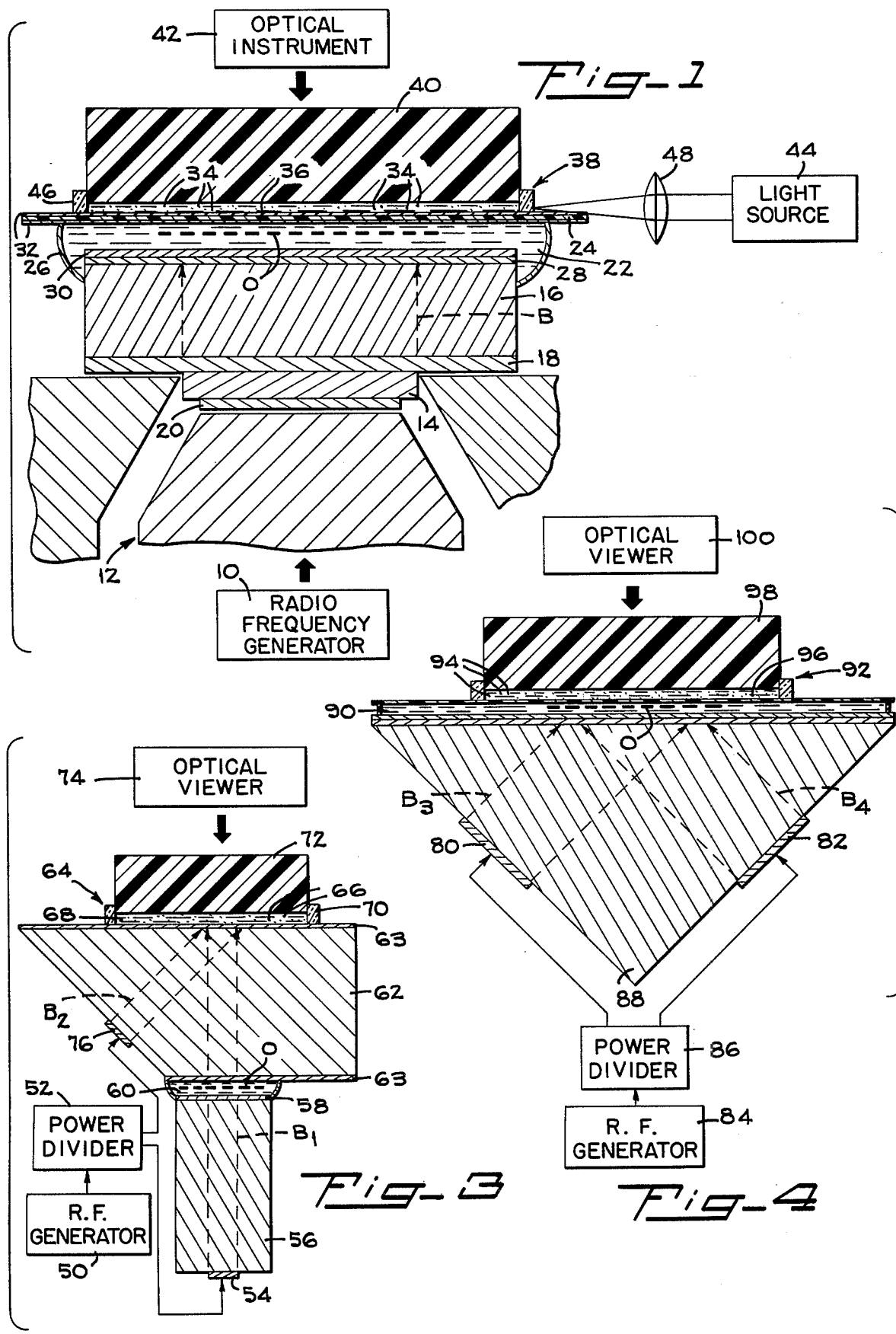

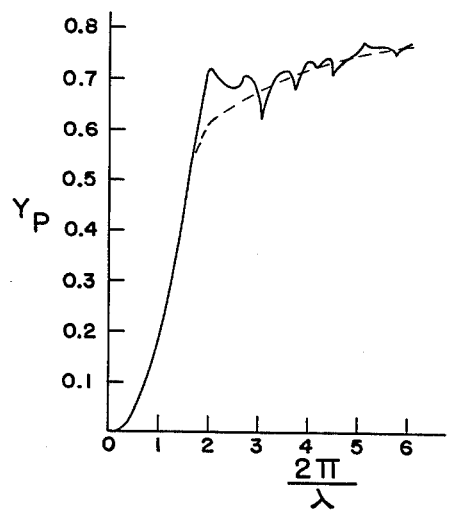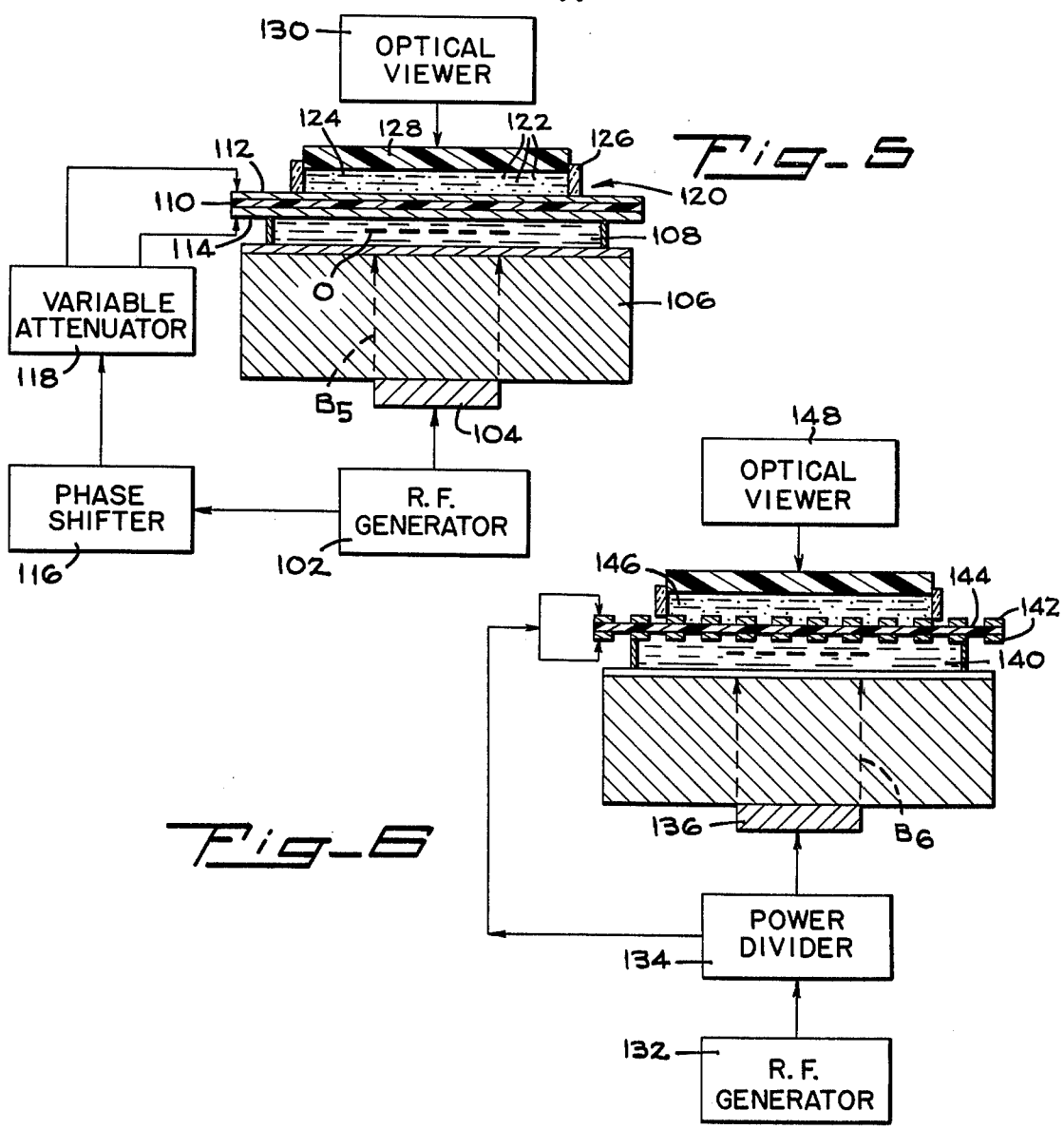

ACOUSTIC IMAGING APPARATUS

FIELD OF THE INVENTION

The present invention relates generally to the production of visible images and more particularly to apparatus for generating images through the utilization of high frequency acoustic wave energy.

BACKGROUND OF THE INVENTION

Conventional imaging systems or microscopes are based on two forms of radiation, electromagnetic waves as in the optical instrument and the electron waves as in the electron microscope.

Optical instruments have been refined over a period of many years to provide more accurate images of even quite small objects such as biological cells. Regardless of such refinements, inherent limitations exist since the optical system basically senses the dielectric properties of the object being imaged. In the first place, resolution, of course, is limited by the wavelength of the visible light (0.5 microns for green light). Some samples are not transparent and therefore inaccessible for viewing. Furthermore, limitations on the contrast sensitivity have appeared and have been but partially overcome by the tedious technique of staining biological specimens to improve such contrast.

Electron microscopes have much greater resolution capabilities but other difficulties arise. The specimen must be viewed in vacuum, a technical problem, and living cells can not be viewed because of the electron bombardment.

The relatively recent development of acoustic wave generation at frequencies approximating 1,000 MHz provides an acoustic wavelength in the neighborhood of one micron and accordingly has suggested itself as a potentially excellent mechanism for the generation of high resolution images and, by way of example, the method described by B. A. Auld et al, "A 1.1 GHz Scanned Acoustic Microscope, " Acoustical Holography 4, Plenum Press (1972) p. 96 has proved not only a high resolution imaging mechanism but also one which provides good contrast sensitivity. However, there has been developed no medium equivalent to a photographic film for recording the image.

SUMMARY OF THE PRESENT INVENTION

Accordingly, it is the general objective of the present invention to provide a novel apparatus employing high frequency acoustic waves in the form of a beam which is directed over the object to provide variations in transmitted acoustic energy which are then detected by means which provides a visible image of the detected object. Such objective can be achieved by apparatus of various types, one of which, for example, can be relatively simple yet extremely effective in its image formation, being arranged to detect variations in acoustic intensity of a plane propagating acoustic wave. More particularly, a standard radio frequency generator is arranged to produce high frequency electromagnetic energy which is delivered to a standard acoustic bulk wave transducer of predetermined configuration so as to generate in an adjoining acoustic propagating medium an acoustic beam which is directed along a predetermined path in which the object to be imaged can be suitably supported depending upon its particular characteristics. The incident acoustic energy which is equalized in its intensity throughout the beam cross-section is absorbed, reflected, or scattered when it impinges upon the object so as to create perturbations of the acoustic energy such as variations in acoustic intensity and phase beyond the object. The intensity variations are then detected by suspension of a plurality of small particles in a liquid or other medium which particles are moved or displaced resultant from the radiation pressure experienced through impingement of the acoustic energy, thus forming an image of the object which can be optically viewed, for example, by a conventional microscope.

Generally, the particles should be quite small since the particle size limits the resolution. However, optimal size will be determined by many factors such as the contrast sensitivity requirements and the characteristics of the suspending liquid or other medium, as will be explained in detail hereinafter. In one apparatus, the particles consisted of small (one micron) polystyrene spheres suspended in water with a slight addition of glycerine to provide a wetting action. Additional contrast sensitivity can be obtained by employing fluorescent particles against which ultraviolet light can be directed and the particles can, in turn, take the form of liquid crystals rather than solid elements so that the term "particle" is to be broadly construed as an element subject to motion and displacement in response to the application of radiation pressure resultant from perturbations of the impinging acoustic energy.

Recognizing that "phase contrast" of acoustic energy may produce improved images, another embodiment of the invention provides an acoustic beam generated as in the first embodiment of the invention and which after perturbation by the object to be imaged, is arranged to intersect with a known phase-related reference acoustic beam, thus basically to provide an acoustic hologram whose wave interference pattern is arranged to generate forces on suspended particles thus to provide the visually-available image.

A single acoustic beam can, in related embodiments of the invention, be generated and directed to the object and the resultant phase variations then compared with phase-related acoustic energy generated by voltages applied through plate or strip electrodes in a piezoelectric film through which the perturbed beam passes and the interference pattern can be then similarly detected by the suspended particles to provide the optical image.

A further embodiment, which may be termed an acoustic quasihologram, provides for the generation of two acoustic beams which intersect in the region of the object to be imaged and the resultant acoustic image interference pattern in turn creates forces on suspended particles to, in a generally analogous fashion, form a visible image of the object.

In each embodiment of the invention it will be understood that because the acoustic imaging depends upon the object's elastic rather than its dielectric properties, a new form of image display is provided and, for example, enables the visible display of optically opaque materials and added details of a biological cell. Furthermore, since the suspended particles can have various properties such as the mentioned fluorescent characteristic, the staining procedures necessary in optical instrumentation can be completely eliminated while assuring high contrast sensitivity.

BRIEF DESCRIPTION OF THE DRAWINGS

FIG. 1 is a diagrammatic central sectional view of an acoustic imaging apparatus constituting one embodiment of the invention, FIG. 2 is a graph explanatory of the forces on a particle resultant from the radiation pressure of applied energy as utilized in accordance with the present invention, FIG. 3 is a central sectional diagrammatic view corresponding to FIG. 1 of a modified apparatus for obtaining acoustic imaging, FIG. 4 is a corresponding illustration of a third embodiment of the invention for obtaining acoustic imaging, and FIGS. 5 and 6 are similar views of yet two other embodiments of the invention.

DETAILED DESCRIPTION OF THE EXEMPLARY EMBODIMENTS OF THE INVENTION with initial reference to FIG. 1, a standard radio frequency generator 10 indicated simply in block diagram form is arranged to generate electromagnetic energy at a relatively high frequency (e.g. 1100 MHz). The energy is introduced through a standard coaxial line input indicated at 12 to a zinc oxide thin film transducer 14 one-quarter wavelength (or odd multiple thereof) in thickness at the operating frequency so as to generate an acoustic beam B which propagates vertically upward through a fused quartz platelet 16 which provides a propagating medium for the generated acoustic beam which is subsequently directed against the object O to be imaged essentially in the near field of the transducer.

More particularly, the thin film of zinc oxide is applied to the acoustic propagating medium across a one-quarter wavelength gold film 18 previously deposited on the highly polished end of the quartz platelet 16 to provide an acoustic transformation between the materials with a minimal amount of energy reflection. It is also preferred that an aluminum coating 20 3,000 A thick be applied over the zinc oxide transducer 14 to provide the desired cross-section of the generated acoustic beam B.

It is to be understood that the transducer art for generating acoustic waves is now well-developed and materials such as lithium niobate or other materials can be employed to generate the acoustic beam and it will as well be understood in accordance with the existing state of the art that other acoustic propagating mediums can be employed. However, for purposes of image formation, it is preferred that the material for acoustic wave propagation have relatively high acoustic isotropy to minimize the wavefront distortions inherent in anisotropic materials. Furthermore, isotropic materials, such as the described quartz, sapphire or other materials, also minimize losses of acoustic energy during propagation thus to minimize the requisite power input.

The object O to be viewed can be conveniently supported in a water cell 22 within the path of the acoustic beam and preferably constitutes a minimal thickness water cell depending upon the object dimensions which is defined between the end of the propagating medium 16 and a thin film 24 of polypropylene or polyester (e.g. MYLAR) stretched across an exterior support ring 26.

Preferably, to provide for efficient transmission of the acoustic energy between the solid fused quartz material and the water, acoustic transformers or anti-reflection coatings 28, 30 of quarter wavelength gold and silicon monoxide are applied over the far or upper end of the quartz. It is also desirable that the surface of the film 24 be coated with a thin (e.g. 300 A) aluminum coating 32 thus to avoid direct optical viewing of the object itself, as will become more apparent hereinafter.

It will be apparent particularly to those skilled in the art that depending upon the characteristics and, in particular, the elastic properties of the object O to be imaged, the incident acoustic energy will be absorbed, scattered or deflected and, as a consequence, beyond the object, perturbations in the acoustic energy such as intensity and phase variations will exist. In accordance with the present invention, such variations are detected by a plurality of very small particles 34 that are supported for movement in the beam path beyond the object O. By way of example, a plurality of one micron polystyrene spheres can be suspended as a thin emulsion, for example, at a 5 percent by volume ratio in a fluid medium 36 which can be water or preferably, a solution containing 90 percent water and 10 percent glycerine to provide a wetting action which enhances the mobility of the particles 34 or polystyrene spheres in the present instance. Because of the variations in the intensity of the acoustic energy in the detection area, radiation pressure will be exerted on the particles (spheres) so as to displace them into a visible pattern or image corresponding to that of the object, thus to form an acoustic energy detector 38. Since the detector is close to the object, diffraction spreading is minimized.

The thin emulsion containing the described particles 34 in the detector 38 is enclosed from above by an acrylic plastic resin (e.g. LUCITE) disc 40 or a microscope glass slide that is supported in spaced relation from the film 24 by a transparent ring 46, the spacing being sufficient to allow upward displacement of the particles 34. The disc 40 (or glass slide) also serves as a transparent medium through which the generated acoustic image can be viewed by suitable optical instrument, generally indicated at 42, and which, for example, may take the form of a microscope.

Illumination of the spheres 34 can be directly obtained from the microscope or other optical instrument 42 utilized and, as previously mentioned, the thin coating 32 of aluminum on the top of the film 24 below the detector 38 eliminates any direct viewing of the object itself and provides a good optical background.

However, in accordance with an additional aspect of the invention, greater contrast sensitivity can be obtained by the simple expedient of directing light laterally through the water in the detector 38 from a suitable light source 44 and lens 48. The coating 32 on the film 24 and the acrylic disc 40 have indices of refraction which are lesser than that of water so as to form therebetween an optical wave guide wherefore only light reflected from the particles will be seen through the optical viewer. Additionally, the particles can be fluorescent and illuminated by ultraviolet light for enhanced contrast.

As previously mentioned, the particles 34 should be very small, such as the one micron polystyrene spheres to achieve good image resolution. With such small particles, several significant forces in addition to the mentioned radiation pressure are exerted thereon. One is obviously gravity acting downwardly an amount dependent on the density and size of the particle. More particularly, with a given material, such as polystyrene, (density - 1.07) gravity varies with the cube of the sphere radius. Additionally, a thermal agitation force exists resultant from Brownian motion which provides a force exerted in random directions on the particle by thermal motion of molecules in the liquid (e.g. water). This force varies inversely with the particle diameter. Thus, this force is greater for small particles while the gravitational force is greater for large particles. Calculations indicate that the two forces are substantially equal for a one micron sphere and such balance allows optimal utilization of the acoustic radiation pressure to move the spheres upwardly to form the visible image. More particularly, the gravitational force is preferably slightly greater than the thermal force so that the particles (one micron polystyrene spheres) will slowly settle but can be moved with a minimal amount of radiation pressure to form the desired image.

Accordingly, the radiation pressure, $F_{rad}$, should at least approximate the gravitational force to produce the required motion and displacement of the particles. The radiation pressure is easily determined by $$F_{rad} = Y_p \pi a^2 Pac/Vs$$

where a is the particle radius
Pac is the acoustic power density
Vs is the acoustic velocity in the liquid, and
Yp is the effective cross-section of the particle The value of Yp varies with the ratio of the particle radius, a, to the acoustic wavelength, $\lambda$, in the liquid and for polystyrene spheres varies as shown in FIG. 2, wherein Yp is plotted as a function of $2\pi a/\lambda$. For a value of $2\pi a/\lambda$ slightly greater than 1, the value of Yp remains rather constant, and thus sets a minimal practical value of the sphere radius, a, for effective imaging. For the polystyrene spheres, a minimal radius of approximately 0.5 micron is thus indicated wherefore the one micron (diameter) spheres were utilized but larger polystyrene spheres can be used if greater acoustic power is available. Smaller particles, with higher density to offset increased thermal agitation can be utilized to increase resolution but obviously greater acoustic power would then be required to form the image. Also, it will be apparent that, as the acoustic power Pac increases, the radiation pressure will increase to form the image more rapidly.

The FIG. 1 arrangement obviously is extremely simple and even in its initial experimental stages has produced image resolution less than 5 microns and a sensitivity of $10^{-3}$ watts per square centimeter. However, it will be apparent that the invention can be incorporated in a variety of structures wherein the redistribution of a number of particles to form an acoustic image can equally well be employed. Furthermore, as will be seen these structures provide certain advantages of "phase contrast" imaging.

By way of example, reference is made to FIG. 3 wherein the same inventive principle is incorporated in a modified embodiment which utilizes a phase-related pair of acoustic beams $B_1$, $B_2$ to generate what may be termed an acoustic halogram. More particularly, radio frequency energy at a relatively high frequency is generated again by a standard radio frequency generator 50 and is delivered to a power divider 52 so that a portion of the power can be delivered to an electroacoustic transducer 54 by means of a coaxial input of the type described in connection with the first embodiment of the invention at the end of a quartz or sapphire acoustic propagating medium 56 thus to generate an acoustic beam $B_1$ therein. Again, in a similar fashion, this acoustic beam $B_1$ is delivered through a suitable anti-reflection coating 58 into a water cell 60 which contains the object O to be imaged and the perturbed acoustic beam $B_1$ the passes along the predetermined path into an additional propagation medium 62 in the form of a prism of isotropic material such as yttrium aluminum garnet (YAG) coated with anti-reflection layers 63 for transmission therethrough into a detector 64 which again takes the form of a plurality of polystyrene spheres 66 or other particles suspended in a thin water film 68 enclosed by an external ring 70 and an acrylic disc 72 through which an optical view can be obtained through an optical viewer 74.

The power divider 52 also delivers the electromagnetic energy into the YAG propagating medium 62 through a transducer 76 to form the second beam $B_2$ to an angle of 45° relative to the acoustic beam $B_1$ transmitted through the object O, thus to create and interference pattern because of the phase differences between the beams $B_1$ and $B_2$ to provide an ultimate intensity variation which effects the displacement of the spheres 66 in the detector or 64 much in the same fashion as described in connection with the first embodiment of the invention.

As yet a further alternative, the image can be formed by the apparatus shown in FIG. 4 which produces essentially what may be termed a quasihologram wherein identical plate transducers 80, 82 are excited from a common radio frequency generator 84 through a power divider 86 so as to generate, at a relative angle of 90°, two acoustic beams $B_3$ and $B_4$ in an acoustic propagating medium 88 in the form, generally, of a prism so that the beams intersect and interfere at the object O which is placed in a water cell 90 adjacent the propagating medium so as to effect phase variations of the interfering beams and generate and acoustic intensity pattern which again is sensed in a similar detector 92 consisting of small particles 94 suspended in water 96, which, in turn, are viewed through an acrylic disc 98 with a standard optical viewer 100 as in the other embodiments of the invention.

In yet another alternative embodiment of the invention diagrammatically depicted in FIG. 5, an acoustic wave interference pattern of two generated acoustic waves is also established but in alignment rather than the angular beam relationship as shown in FIGS. 3 and 4. More particularly, a radio frequency generator 102 delivers its electromagnetic output to an electroacoustic transducer 104 which generates an acoustic beam $B_5$ that traverses and acoustic propagating medium 106 and impinges on the object O to be imaged in a water cell 108 on the far side of the medium in the fashion described in detail hereinabove relative to the FIG. 1 embodiment. However, after passing the object O, the perturbed beam $B_5$ is phase compared with an acoustic wave generated in a thin film 110 of a piezoelectric material such as polyvinyl fluoride or polyvinylidene fluoride which closes the top of the water cell 108. To generate the acoustic wave in the film 110, plate electrodes 112, 114, which may constitute thin films of aluminum, nickel or other metal, have applied thereacross a radio frequency voltage received from the same radio frequency generator 102 after a phase shift of 180° in a standard phase shifter 116 and controlled attenuation of the energy in a variable attenuator 118. The attenuation is adjusted to compensate for the losses of the acoustic energy in the beam transit of the propagating medium 106 the transducer 104 and the water cell 108 so that the two waves are equalized in energy. Then since the two waves are 180° out of phase, in the absence of an object, there will be a complete cancellation of acoustic energy. However, with the object O present in the path of the first beam $B_5$, the resultant phase perturbation of the acoustic energy will provide a phase-interference pattern which will produce an image in a detector 120 which is the same as that described in the other embodiments of the invention, that is, a plurality of small particles 122 suspended in water 124 or other liquid. The detector 120 is closed by an exterior ring 126 and a transparent top plate 128 of acrylic so that the image can again be viewed by a suitable optical viewer 130.

A further embodiment shown in FIG. 6 is functionally similar to that shown in FIG. 3 in that a phase comparison is made but is structurally more similar to the FIG. 5 arrangement. Power from a radio frequency generator 132 is delivered to a power divider 134, one output of which is applied to a transducer 136 to generate an acoustic beam $B_6$ which traverses an acoustic propagating medium 138 to impinge on an object O in a water cell 140 which effects a phase perturbation of the acoustic energy. This energy is phase compared with that generated in a plurality of electrodes 142 in the form of metal fingers spaced one-half wavelength apart on a thin piezoelectric film 144 by application of power from the mentioned power divider 135. The resultant acoustic energy is imaged in a detector cell 146 and observed by an optical viewer 148 in a manner analogous to the other embodiments of the invention.

It will be apparent that yet further modifications and alterations can be envisioned without departing from the spirit of the present invention and accordingly the foregoing descriptions of several embodiments is to be considered as purely exemplary and not a limiting sense and the actual scope of the invention is to be indicated only the appended claims.

What is claimed is:

1. Acoustic imaging apparatus which comprises
    means for generating an acoustic wave beam along a predetermined path,
    means supporting an object to be imaged in said acoustic beam path,
    a plurality of visible particles suspended throughout a fluid medium for displacement in the beam path beyond the object in proportion to the intensity of radiation pressure resultant from the acoustic energy,
    said particles being suspended in a thin layer of liquid disposed between enclosing layers of material whose optical indices of refraction are less than that of the suspending liquid, to define an optical waveguide and
    means for directing light through said liquid layer between said enclosing material layers,
    whereby essentially only light reflected from said particles will form an optical image of said object.

* * * * *